United States Patent
Kraemer et al.

(10) Patent No.: US 7,315,752 B2
(45) Date of Patent: Jan. 1, 2008

(54) METHOD AND DEVICE FOR DETERMINING A LIGHT TRANSPORT PARAMETER IN A BIOLOGICAL MATRIX

(75) Inventors: Uwe Kraemer, Ilvesheim (DE); Heinz-Michael Hein, Darmstadt (DE); Marcus Hermann, Mannheim (DE)

(73) Assignee: Roche Diagnostics GmbH, Mannheim (DE)

( * ) Notice: Subject to any disclaimer, the term of this patent is extended or adjusted under 35 U.S.C. 154(b) by 417 days.

(21) Appl. No.: 10/499,109

(22) PCT Filed: Dec. 7, 2002

(86) PCT No.: PCT/EP02/13884

§ 371 (c)(1),
(2), (4) Date: Aug. 26, 2004

(87) PCT Pub. No.: WO03/055382

PCT Pub. Date: Jul. 10, 2003

(65) Prior Publication Data

US 2005/0002031 A1    Jan. 6, 2005

(30) Foreign Application Priority Data

Dec. 22, 2001 (DE) ................ 101 63 972

(51) Int. Cl.
*A61B 5/00* (2006.01)
(52) U.S. Cl. ............. 600/316; 600/310; 600/322; 600/344
(58) Field of Classification Search ........ 600/309, 600/310, 316, 322, 344, 473, 476
See application file for complete search history.

(56) References Cited

U.S. PATENT DOCUMENTS 5,452,723 A    9/1995  Wu et al.

(Continued)

FOREIGN PATENT DOCUMENTS

DE    196 30 381 A1    5/1997

(Continued)

OTHER PUBLICATIONS

T.J. Farrell et al. "A diffusion theory model of spatially resolved, steady-state diffuse reflectance for the noninvasive determination of tissue optical properties in vivo", Med. Phys. 19, pp. 879-888 (1992).

(Continued)

*Primary Examiner*—Eric F. Winakur
*Assistant Examiner*—Jack Lin
(74) *Attorney, Agent, or Firm*—Baker & Daniels LLP (57) ABSTRACT

A method for the selective determination of the scattering index $\mu_s$ of a scattering biological matrix, in particular for the purpose of non-invasive determination of the concentration of glucose in the skin, by means of detection measurements, in each of which light in the form of primary light (9) is irradiated into the biological matrix (5) and an intensity measurement value of secondary light (12) exiting at a detection site (33-40) that is located at different measuring distances ($\rho$) from the respective light irradiation site (10) during the detection measurements is measured. In order to improve the quality and selectivity of the determination of $\mu_s$, the primary light is irradiated obliquely at an angle between 5° and 85° using a contacting light-guiding element. In at least two detection measurements, the measuring distance ($\rho$) between the respective light irradiation site (10) and the respective detection site (33-40) corresponds to no more than five times the mean free path length of the light propagating in the biological matrix.

20 Claims, 2 Drawing Sheets

U.S. PATENT DOCUMENTS

| | | |
|---|---|---|
| 5,551,422 A | 9/1996 | Simonsen et al. |
| 5,630,423 A | 5/1997 | Wang et al. |
| 5,676,143 A | 10/1997 | Simonsen et al. |
| 5,770,454 A | 6/1998 | Essenpreis et al. .......... 436/164 |
| 5,825,488 A | 10/1998 | Kohl et al. ................. 356/342 |
| 5,867,807 A | 2/1999 | Yamada ....................... 702/30 |
| 5,893,364 A | 4/1999 | Haar et al. .................. 600/310 |
| 6,041,247 A * | 3/2000 | Weckstrom et al. ......... 600/323 |
| 6,219,566 B1 | 4/2001 | Weersink .................... 600/317 |
| 2002/0107448 A1* | 8/2002 | Gandjbakhche et al. .... 600/476 |
| 2004/0152089 A1 | 8/2004 | Kraemer et al. |

FOREIGN PATENT DOCUMENTS

| | | |
|---|---|---|
| DE | 101 10 599 A1 | 9/2002 |
| EP | 0760091 | 3/1997 |
| EP | 0 843 986 A2 | 5/1998 |
| GB | 2075668 A * | 11/1981 |
| WO | WO 94/10901 | 5/1994 |
| WO | WO 01/09589 A1 | 2/2001 |

OTHER PUBLICATIONS

R.C. Haskell et al. "Boundary conditions for the diffusion equation in radiative transfer", J. Opt. Soc. Am. A, 11, pp. 2727-2741 (1994).

S.A. Prahl et al. "A Monte Carlo model of light propagation in tissue", SPIE Institute Series, IS 5; pp. 102-111, (1989).

Guillermo Marquez et al. "White light oblique incidence reflectometer for measuring absorption and reduced scattering spectra of tissue-like turbid media", Optics Express, pp. 454-460, (1997).

Sao-Pow Lin et al. "Measurement of tissue optical properties by the use of oblique-incidence optical fiber reflectometry", Applied Optics, Opt. Soc. America, vol. 36, No. 1 pp. 136-143, (1997).

* cited by examiner

METHOD AND DEVICE FOR DETERMINING A LIGHT TRANSPORT PARAMETER IN A BIOLOGICAL MATRIX

FIELD OF THE INVENTION

The invention refers to a method for the selective determination of a light transport parameter which is characteristic of the light scattering in a biological matrix, in particular for the non-invasive determination of the concentration of an analyte influencing the light scattering in a biological matrix, in particular of glucose in the biological matrix. A suitable device for this purpose is also the subject of the invention.

BACKGROUND OF THE INVENTION

The term "biological matrix" denotes a body fluid or a tissue of a living organism. Biological matrices for the purposes of the invention are optically heterogeneous, i.e. they contain a large number of scattering centers, at which incident light is scattered. In the case of biological tissue, in particular skin tissue, the scattering centers are formed by the cell walls and other solid components contained in the respective tissue. Body fluids, in particular blood, also constitute optically heterogeneous biological matrices since they contain particles at which light is multiply scattered.

The transport of light in a biological matrix is essentially determined by the scattering of light at scattering centers contained in the matrix, and by optical absorption. Physical parameters which describe these two properties quantitatively are called light transport parameters (scattering parameters and absorption parameters). In this context, a scattering parameter is primarily the scattering coefficient, $\mu_s$, and an absorption parameter is primarily the absorption coefficient, $\mu_a$. However, within the scope of the invention these parameters need not be determined quantitatively in the customary units. Rather, it is the objective of the invention to determine in a reproducible and selective manner a parameter that describes the optical scattering in the biological sample independent of its optical absorption. Hereafter the scattering coefficient, $\mu_s$, shall be referred to as an example of a scattering parameter without limiting the general applicability of the invention.

The selective determination of the scattering coefficient is of general interest in medicine, since important diagnostic information can be derived from the interaction of light with skin tissue and other biological matrices. As an example, it is possible in dermatology to characterize skin properties by this means.

Particularly significant is the investigation of the scattering behavior of a biological matrix for the purpose of determining, in a non-invasive manner, the concentration of analytes influencing the scattering of light, in particular glucose. The relationship between the glucose concentration and the scattering of light in biological matrices is described in EP 0659055 B1. As is illustrated therein (and in numerous other publications concerned with the analysis of glucose in the human body), the quality of diabetic therapy crucially depends on a frequent, preferably continuous, determination of the time course of the blood sugar level in the body of diabetics. Thereby severe secondary damage due to diabetes mellitus, such as loss of eyesight or severe circulatory disorders possibly leading to a need for amputation of limbs, can be prevented. The desirable continuous monitoring of the blood sugar level is not feasible with conventional invasive methods (in which a droplet of blood is removed from the patient's body and analyzed with one of the analytical systems that are currently available at good quality and favorable costs). Consequently, there have been numerous attempts to determine the concentration of glucose by a non-invasive approach. A more detailed overview is provided in the European patent referred to above.

In the method described in EP 0659055 B1, a plurality of "detection measurements" is performed to determine a glucose value, wherein light is irradiated as primary light into the biological matrix at a defined light irradiation site, the light propagates in the biological matrix along a light path, and an intensity measurement value of the secondary light exiting at a defined detection site is measured. The glucose concentration is determined from the dependence of the intensity measurement value on the measuring distance between the respective light irradiation site and the respective detection site by means of an evaluation algorithm and a calibration.

The surprising finding that a measuring method of this kind can be used to measure the change over time of the glucose concentration in skin tissue or other biological matrix, is in EP 0659055 B1 explained by the fact that the change in the refractive index of the liquid contained in the matrix caused by a changing glucose concentration (although small) leads to a change in light scattering that can be used to determine the glucose concentration by investigating the scattering behavior of light in compliance with the further instructions provided in the European patent. According to a preferred embodiment, the influences of absorption and scattering are separated in the evaluation step by analyzing the intensity distribution of the secondary light as a function of the distance of the detection site from the light irradiation site.

Similarly, it has been discussed in the scientific literature for a substantial period of time to determine $\mu_a$ and $\mu_s$ from the dependence $I(\rho)$ of the intensity, I, of the secondary light from the measuring distance, $\rho$, (hereinafter referred to as "intensity profile"). The theoretical basis is provided by diffusion theory and numerical statistical methods (Monte Carlo calculations). The theory provides a model for the description of the propagation behavior of light in a scattering matrix, in which a mathematical relationship is established between the intensity profile, $I(\rho)$, and the model parameters used in the model (mainly the light transport parameters, $\mu_a$ and $\mu_s$, and the intensity of the incident primary light, $I_0$. In principle, it is feasible to determine the light transport parameters by performing a fit, in which the intensity profile calculated theoretically is optimally fitted to the experimental results by varying the parameters of the model. In this context, reference is made to the following publications:

1) T. J. Farrell et al.: "A diffusion theory model of spatially resolved, steady-state diffuse reflectance for the noninvasive determination of tissue optical properties in vivo", Med. Phys. 19, 879 to 888 (1992)
2) R. C. Haskell et al.: "Boundary conditions for the diffusion equation in radiative transfer", J. Opt. Soc. Am. A, 11, 2727 to 2741 (1994).

Although the measured values and the theoretical calculations are reported to agree quite well in these references, these methods never attained any practical significance for the determination of the glucose concentration in a biological matrix.

The patent literature describes a number of methods aiming to determine $\mu_a$ and $\mu_s$ in a biological matrix in order to obtain therefrom analytical data for medical purposes, in particular for the determination of the glucose concentration.

3) According to EP 0760091 B1, at least two frequency domain measurements each are performed for at least two different measuring light paths, the measurements including the determination of the phase shift of the secondary light as compared to the primary light and the determination of an intensity measurement value (namely the DC intensity or the AC intensity). An absorption parameter and/or scattering parameter is then derived from these at least four measuring values. Since frequency domain measuring procedures operate with light modulated in the GHz range they require extensive measuring technological resources.)

4) EP 0774658 A2 describes a method, in which the scattering properties of a biological matrix are analyzed by varying the reflection properties at the surface of the matrix. As an example, the contact surface of the measuring head used for the measurement can comprise different partial areas with different reflectivities. By this means, the reflection properties are varied at least twofold for two measuring distances. The publication illustrates that the resulting at least four measuring values can be used to separate absorption and scattering (either on the basis of diffusion theory or by empirical-numerical means). This method also is relatively resource-consuming. Moreover, it is difficult to achieve the level of reproducibility of the measuring values that is required for the analysis of the glucose concentration.

5) German patent application 10110599.1, dated Mar. 6, 2001, published after the priority date of this patent application, describes a specific evaluation algorithm for the determination of the scattering coefficient from a plurality of detection measurements. The relative change of the intensity profile over time is used to calculate a time derivative value as an intermediary value to simplify the separation of the influences of the model parameters (in particular of the absorption coefficient and the scattering coefficient), and thereby achieve improved accuracy in the determination of the scattering coefficient by simple means.

SUMMARY OF THE INVENTION

On the basis of this state of the art, it is an object of the present invention to selectively determine in a biological matrix the scattering coefficient, $\mu_s$, (or other parameter describing the scattering of light) or the concentration of an analyte influencing the scattering of light in the biological matrix by means of a method that is characterized by simple use, low equipment requirements, and high accuracy.

This object is achieved according to a first main aspect of the invention by a method for the selective determination of a light transport parameter that is characteristic of the light scattering in a biological matrix and/or for the non-invasive determination of the concentration of an analyte influencing the light scattering in the biological matrix, in particular of glucose in the biological matrix, comprising at least three detection measurements, in each of which light in the form of primary light is irradiated into the biological matrix at a light irradiation site and then propagates in the biological matrix along a light path, and an intensity measurement value of secondary light exiting at a detection site located at different measuring distances from the respective light irradiation site in the plurality of detection measurements is measured, and an evaluation step, in which the light transport parameter that is characteristic of the light scattering in the biological matrix is derived by means of an evaluation algorithm from the intensity measurement values measured in the detection measurements, in which the primary light is irradiated by means of a light-guiding element contacting the surface of the biological matrix at the light irradiation site, the primary light is irradiated into the biological matrix obliquely at the light irradiation site at a light irradiation angle between 5° and 85° with regard to a normal onto the surface, and, in at least two detection measurements, the measuring distance between the respective light irradiation site and the respective detection site corresponds to no more than five times the mean free path length of the light propagating in the biological matrix.

Experimental evaluation of a measuring set-up according to the invention with the combination of these features has shown that it allows the easy, accurate, selective determination of the scattering coefficient. Most importantly, in-vivo tests at the surface of the skin for the determination of the glucose concentration result in an improved correlation between the measuring value and analytical values determined by conventional (invasive) means.

Irradiating the light at an oblique angle results in a small depth of penetration of the primary light into the biological matrix while the light-path is sufficiently long. In the scope of the invention it was noted that this results in an improvement of the homogeneity of the tested tissue and this again contributes to a more accurate measuring result. In addition, an improved correlation between the glucose concentration detected in the skin and the glucose concentration detected in the blood was achieved.

Taken by itself, it is a known design feature to irradiate the light at an oblique angle. For instance in U.S. Pat. No. 5,630,423 a beam of primary light is irradiated at an angle between 5° and 85° in order to obtain from the resulting shift of the center of the intensity distribution of the secondary light an information concerning the scattering properties of the sample. From the distribution curve of the intensity (denoted M in FIG. 3 of the US patent), a mean value curve C is derived which is shifted horizontally by $\Delta x$ with respect to the origin. The US patent describes a mathematical relationship between this $\Delta x$ and $\mu_s$, by means of which the reduced scattering coefficient $\mu_s'$ is calculated. Therefore, irradiation of the light at an oblique angle serves a completely different purpose than in the present invention.

The invention differs from the method of the US patent also in that therein the primary light is irradiated without contact using a free beam set-up and the secondary light is detected (also without contact) by means of a CCD camera. The analysis is based on measurements with a measuring distance of up to more than 1.3 cm. In skin tissue, this corresponds to almost 20 times the mean free path length (approx. 0.7 mm). In contrast, it is a requirement of the method according to the invention that the primary light is irradiated by means of a light-guiding element contacting the surface of the biological matrix, for example the surface of the skin. Also, the detection of the secondary light is preferably performed with a light-guiding element contacting the matrix.

The term, "light-guiding element", shall comprise various different designs, for instance in the form of light-guiding rods or fibers. A transparent section ("window") in a plate closing a measuring head where it contacts the skin (skin contact plate) is also a light-guiding element in this context. It is required in any case, that the light is transported in a transparent solid body at least on the final section of the light path before entering the matrix, said transparent solid body contacting the surface of the biological matrix.

For the function of the present invention it is necessary that at least two, preferably at least three, and particularly preferably at least four, of the detection measurements performed in the evaluation step to determine the scattering coefficient are performed at measuring distances which are at most five times the mean free path length. It is particularly preferred to use in the evaluation step exclusively intensity measurement values resulting from detection measurements, in which the measuring distance is no larger than ten times the mean free path length. In the skin, the stated limits of the measuring distance correspond to about 3.5 mm and 7 mm, respectively.

A further development of the method described in U.S. Pat. No. 5,630,423, is described in G. Marquez et al. "White light oblique incidence reflectometer for measuring absorption and reduced scattering spectra of tissue-like turbid media", OPTICS EXPRESS, 1997, 454-460.

In this method, the light is irradiated and detected at an angle of 45°, both by means of light-guiding fibers. The light is irradiated simultaneously with a wavelength bandwidth of 256 nm. Under additional assumptions, this purportedly allows not only $\mu_s$, but also $\mu_a$, to be determined from $\Delta x$ and the direction of the beam (incident angle $\alpha$).

The determination of the scattering coefficient in the evaluation step is in the cited references based on diffusion theory. In contrast, a numerical simulation is preferably used in the invention. Here, the theoretical dependence of the intensity I of the secondary light from the measuring distance $\rho$ and the light transport parameters $\mu_a$ and $\mu_s$ is calculated by means of a numerical simulation, for instance a Monte Carlo calculation, and a fit is performed in which the light transport parameters are varied such that the numerical simulation optimally describes the experimentally determined values of the intensity I as a function of the measuring distance $\rho$. by using a numerical simulation it becomes feasible to analyze measuring signals obtained at very short measuring distances of one to a few mean free path lengths. In this range diffusion theory does not provide correct predictions.

From the resulting values of the scattering coefficient, a corresponding information concerning the concentration of an analyte influencing the scattering of light in the biological matrix can be derived by calibration. Alternatively, it is also possible to determine a direct numerical correlation between the measured intensities and the analyte concentration (by means of calibration) without explicitly calculating a light transport parameter that is characteristic of the scattering of light.

According to a second main aspect of the invention, which is preferably used in combination with the first main aspect, but can also be used to independently thereof, an evaluation algorithm with the following partial steps is performed in the evaluation step:

a) determining by means of a numerical simulation for a typical value of optical scattering ($\mu_{s,MC}$) the theoretical dependence of the intensity (I) of the secondary light from the measuring distance ($\rho$) and the optical absorption ($\mu_a$);
b) storing the result of the simulation as a lookup table by which an intensity value (I($\rho$, $\mu_a$)) is assigned to predetermined values of the measuring distance ($\rho$) and optical absorption ($\mu_a$);
c) determining the parameter ($\mu_s$) which is characteristic of the light scattering in the biological matrix by means of a fit procedure, in which for a plurality of different values of the light transport parameters ($\mu_a$, $\mu_s$) characterizing the light transport in the biological matrix the dependence of the intensity (I) on the measuring distance ($\rho$) is calculated and the result is compared to the intensity measurement values measured in the detection measurements in order to determine those values of the light transport parameters ($\mu_a$, $\mu_s$) at which an optimal agreement of the calculated dependence of the intensity (I) on the measuring distance ($\rho$) and the respective intensity measurement values is achieved, wherein step c) comprises the following steps:

c1) calculating a scaling factor (s) from the relation of any selected optical scattering value ($\mu_s$) to the typical optical scattering ($\mu_{s,MC}$) used in step a);
c2) converting the independent variables ($\rho$, $\mu_a$) of the lookup table stored in step b) by means of the scaling factor (s);
c3) calculating the dependence of the intensity (I) on the optical absorption ($\mu_a$) and the measuring distance ($\rho$) at the selected optical scattering value ($\mu_s$) by means of the converted variables on the basis of the values stored in the lookup table.

By applying this evaluation algorithm it is possible to use the analysis on the basis of numerical simulation procedures even in relatively small analysis instruments equipped with relatively little computing power. This applies in particular to mobile analysis instruments such as those used by diabetics to regularly determine their glucose levels. Preferably steps a) and b) of the evaluation algorithm are performed by means of a powerful computing system outside the mobile analysis instrument, whereas step c) including partial steps c1 to c3 can be performed in the mobile analysis instrument that is equipped with considerably less computing power.

The invention is illustrated hereafter on the basis of the exemplary embodiments shown in the figures. The features described therein may be used individually or in combination in order to generate further preferred embodiments of the invention. In the figures:

DETAILED DESCRIPTION OF EMBODIMENTS OF THE INVENTION

Figure 1:
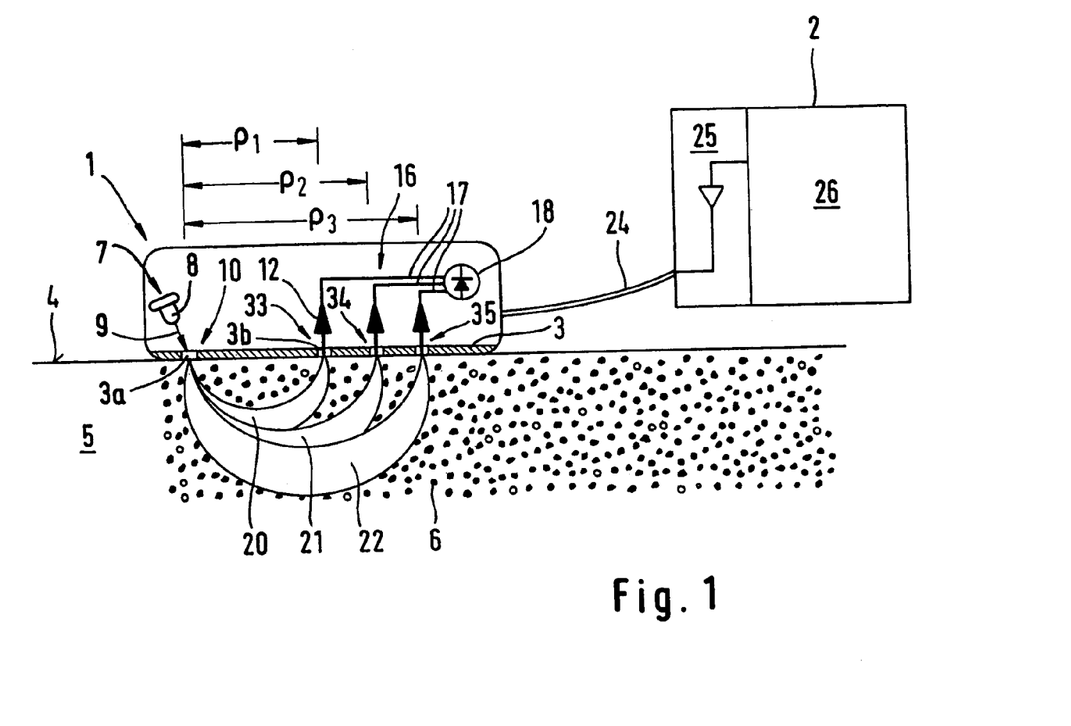
FIG. 1 shows a schematic cross-sectional view of a device for optical analysis of a biological matrix.

The device for the selective determination of $\mu_s$ in a biological matrix shown in FIG. 1 in a highly schematic manner essentially consists of a measuring head 1 and a signal processing and evaluation unit, 2. Hereinafter, reference will be made to skin tissue as an example of the biological matrix.

Measuring head 1 is placed with the bottom side of a skin contact plate 3 against a surface 4 of the skin 5 containing a large number of scattering centers 6. Light irradiation means 7 with a photodiode 8 are located inside measuring head 1 and serve to irradiate primary light (arrow 9) through a light irradiation window 3a at a light irradiation site 10 into the biological matrix 5.

Secondary light symbolized by arrows 12 and exiting at three detection sites 33, 34, and 35, which are defined by detection windows 3b of skin contact plate 3, is detected by detection means which are jointly denoted 16. In the embodiment shown, the detection means 16 enclose light-guiding fibers 17 guiding the secondary light of all three detection sites to a common photodetector 18 (for example a photodiode, in particular an Avalanche photodiode 18). Light-guiding fibers 17 contain optical switches (not shown) to provide for the required separation of the intensity measurement values of the three detection sites.

The light paths along which the light irradiated into biological matrix 5 propagates between the light irradiation site 10 and the detection sites 33 to 35 are denoted 20 to 22 and are shown in a symbolic manner in FIG. 1. Due to the scattering in the biological matrix, it is self-evident that no sharply delineated light paths can be indicated. However, it can be assumed that the majority of the photons detected as secondary light propagate approximately on a curved light path—similar to the one shown—the mean penetration depth increasing with increasing measuring distance ρ between light irradiation site 10 and detection site 33 to 35.

The output signal of the photodetector is transmitted by means of a cable 24 to an electronic signal processing unit 25 in which it is amplified, processed, and digitalized in known manner such that at the output of the unit digital intensity measurement values are provided, which correspond to the intensity of the secondary light exiting at detection sites 33 to 35.

Up to this point, the device shown is conventional and need not be discussed in further detail. Both the light irradiation means and the detection means can be implemented in the form of light emitters and light-sensitive elements that are integrated into skin contact plate 3 or by means of light-guiding fibers guiding the light from a more distant light emitter to skin contact plate 3 or from this plate to a photodetector. Any embodiment according to the invention requires the presence of a light-guiding element contacting surface 4.

This includes, for example, a design in which the transparent housing of a photodiode is integrated into skin contact plate 3.

The different measuring distances can be provided by means of different combinations of light irradiation and detection sites. In particular, the three measuring distances $\rho_1$, $\rho_2$, and $\rho_3$ shown in FIG. 1 can also be implemented, in principle, by irradiating the light at three different light irradiation sites and measuring at one detection site.

Further details concerning the design of the measuring head, performance of the detection measurements, and measurement of the intensity measurement values for different measuring distances are illustrated in the published state of the art. In particular, reference can, in this context, be made to EP 0659055 B1 in which different set-ups and designs of the light irradiation means and detection means are described. The content of this document is incorporated herein by reference.

In any case, measuring head 1 and electronic signal processing unit 25 are provided such that intensity measurement values are determined by electronic signal processing unit 25 for the measuring distances that are possible with the respective measuring head (the measuring distances $\rho_1$, $\rho_2$, and $\rho_3$ in the example shown) and transmitted in digital form to electronic evaluation unit 26. As is common for digital devices, electronic evaluation unit 26 contains a microcomputer which performs the calculations described below.

Figure 2:
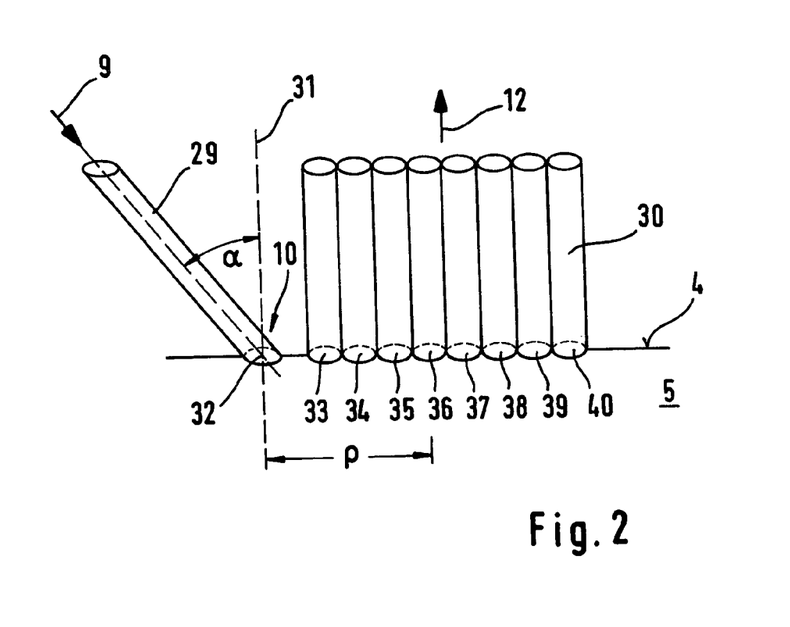
FIG. 2 shows a schematic perspective view of the light-guiding elements used for irradiating the primary light and detecting the secondary light, according to a first embodiment of the invention.

FIG. 2 illustrates the geometric arrangement of the light-guiding elements according to a first preferred embodiment of the invention. The primary light 9 is irradiated into the skin 5 by means of an irradiating light-guiding element 29 whose optical axis is inclined at an angle α with respect to a normal 31 on surface 4. This angle is about 40° in the case shown (but more generally can be between 5° and 85°). Light-guiding element 29 can consist of one and a plurality of light-guiding fibers. Its front surface 32 rests against surface 4 of the skin 5 and is provided with an oblique cut such that it rests flat against surface 4 at the given angle of inclination α.

In the embodiment shown in FIG. 2, the secondary light 12 is detected by means of eight detection light-guiding elements 30 which contact the surface 4 of the skin at light detection sites 33 to 40. The detection sites 33 to 40 are separated from light irradiation site 10 by measuring distances ρ (the measuring distance of detection site 36 is shown). Light-guiding elements 30 are oriented perpendicular to surface 4 (and therefore parallel to normal 31) and consequently detect secondary light exiting from surface 4 in the direction of normal 31.

Figure 3:
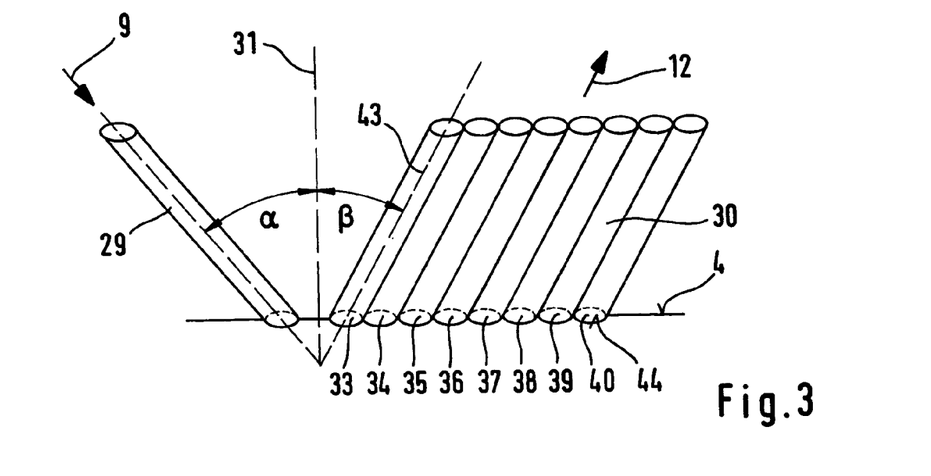
FIG. 3 shows a schematic perspective view of the light-guiding elements used for irradiating the primary light and detecting the secondary light, according to a second embodiment of the invention.

The embodiment shown in FIG. 3 differs from FIG. 2 with regard to the direction of detection β in which detection light-guiding elements 30 detect the secondary light exiting from surface 4 at detection sites 33 to 40. The detection direction runs at an oblique angle β with regard to surface 4, i.e. angle β between the detection direction (optical axis 43 of detection light-guiding elements 30) and normal 31 is not zero and preferably is between 5° and 85°. Preferably, angle β is oriented such that the detection direction 43 runs towards light irradiation site 10, i.e. angles α and β are on different sides of normal 31. Like the front surface 32 of the irradiating light-guiding element, the front surfaces 44 of detection light guides 30 are polished to be oblique such that they rest flat against surface 4 of skin 5.

With this type of arrangement the effective measuring volume of the detector, i.e. the volume through which the light detected by the detector propagates with high probability, is shifted upwards, towards the surface of the skin, as compared to perpendicular detection. This can be useful in order to make the measurement more sensitive in certain layers of the skin.

Figure 4:
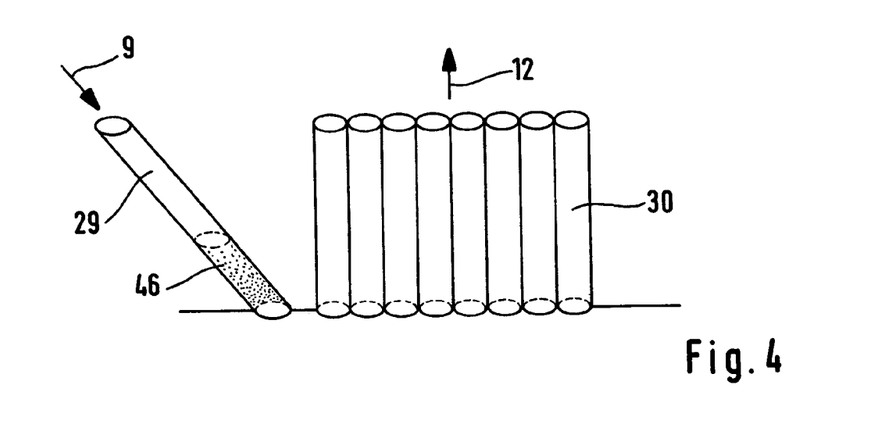
FIG. 4 shows a schematic perspective view of the light-guiding elements used for irradiating the primary light and detecting the secondary light, according to a third embodiment of the invention.

In order to obtain a more exactly defined beam profile at light irradiation site 10 when using small light irradiation angles (angles α in excess of approx. 30°), it can be useful to focus the primary light 9 by means of a GRID lens 46 which in the embodiment shown in FIG. 4 is integrated into incident light-guiding element 29.

Several different means can be used for providing the primary light 9 and for transporting the secondary light 12. Also light-guiding elements 29 and 30 can be implemented very differently. For the scope of the present invention it is only important that at least the light irradiation angle α, but preferably also the detection angle β, is within a range of angles between 5° and 85° with regard to a normal 31 on surface 4, that light-guiding elements 29, 30 contact surface 4, and that the measuring distances ρ are very small as compared to the methods known hitherto, preferably within the limits specified above.

Figure 5:
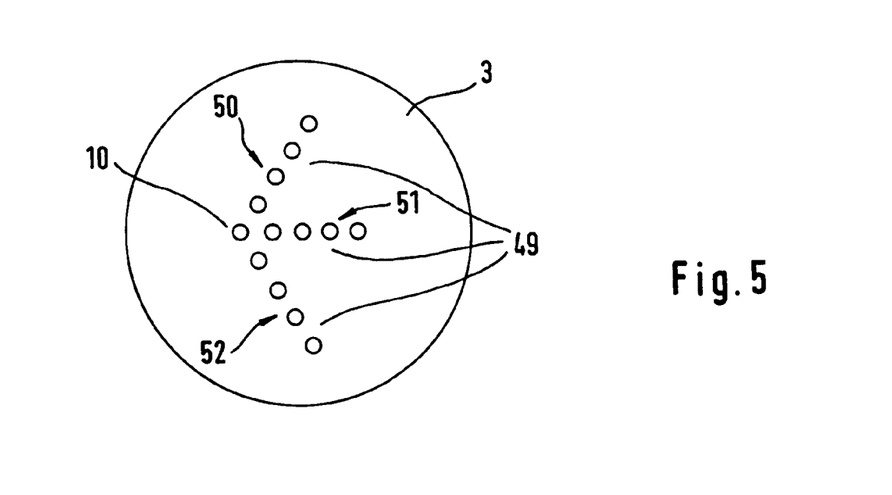
FIG. 5 shows a plan view onto the bottom side of a measuring head according to another preferred embodiment.

FIG. 5 shows the bottom side of a skin contact plate 3 of a measuring head, in which, according to another preferred embodiment, the secondary light is detected at a plurality of detection fields 50, 51, and 52, each of which comprises a plurality of detection sites 49. The detection direction of the plurality of detection sites of a detection field is uniform, but differs between the plurality of detection fields 50, 51, and 52. In the case shown, the detection means of detection fields 50, 51, and 52 are all facing one detection site 10 from various directions. A plurality of detection fields facing a common light irradiation site 10 from various directions can contribute to improved photon statistics and, by way of redundancy, to a more robust measuring result. This reduces errors due to inhomogeneities of the surface of the skin (for example hair roots or sweat glands).

According to an advantageous further development, the light-guiding elements 29, 30 can be integrated into a fiber plate resting against the skin. The use of a fiber plate for measuring a light transport parameters described in U.S. Pat. No. 5,893,364. In order to irradiate the light into the skin at an oblique angle, the fiber plate can be provided with a bore hole at an oblique angle, into which an incident light-guiding element can be inserted. Alternatively, a deflection prism can be placed in the beam path in order to direct the light into the desired direction. The detection at a plurality of detection sites can be performed through the fibers of the fiber plate, as described in the US patent referred to above. An oblique detection direction can be implemented by cutting the optical fiber plate at a desired angle oblique to the direction of its light-guiding fibers.

Hereafter, the evaluation algorithm that is used according to the second main aspect of the invention is illustrated in more detail.

In the absence of optical absorption, scattering can be described by the following scaling equation:

$$I(\rho, \mu_s, \mu_a = 0) = \left(\frac{\mu_s}{\mu_{s,MC}}\right)^3 \times I\left(\rho \frac{\mu_s}{\mu_{s,MC}}, \mu_{s,MC}, \mu_a = 0\right) \quad (1)$$

This assumes the matrix is isotropic such that the intensity profile depends only on the distance from the light irradiation site, but not from the azimuth angle $\phi$. $\mu_{s,MC}$ is a fixed value of the scattering coefficient on which the scaling is based.

According to equation (1) the intensity profile $I(\rho)$ is scaled, in the absence of absorption, by the mean free path length $1/\mu_s$. The path length of the photons in a scattering matrix is scaled by the same factor in the absence of absorption.

With regard to optical absorption, according to the law of Lambert-Beer the absorption probability of the photons depends only on the absorption coefficient and the length of the path of the photon within the matrix. The intensity profile due to absorption is therefore an exponentially declining function, though it must be taken into consideration that the coefficients of this function depend on $\mu_s$ and $\rho$. The following equation can be used to describe the dependence of the intensity profile on the absorption:

$$I(\mu_a) = I_0 \exp(-a\mu_a - b\sqrt{\mu_a}) \quad (2)$$

A lookup table is calculated in steps a) and b) of the evaluation algorithm on the basis of a numerical simulation. A Monte Carlo simulation is particularly suitable for this purpose. This is a standard simulation method which is particularly used in biomedical optics. It is described, for example, in the following publication:

S. A. Prahl et al. "A Monte Carlo model of light propagation in tissue", SPIE Institute Series, IS 5; 102-111, 1989

In a Monte Carlo simulation of this type, the paths of a large number of photons (typically on the order of approx. $10^7$) are simulated by determining for each photon a random path through the matrix on the basis of the laws governing its propagation in a scattering and absorbing matrix. In particular, this includes the determination of the location where the photon exits from the matrix and the length of its path through the matrix. For a certain set of light transport parameters and a certain geometry of the matrix, this results in an intensity profile $I(\rho)$ of the light exiting at the surface.

The Monte Carlo simulation is based on a typical scattering coefficient value $\mu_{s,MC}$ and values for the mean refractive index n, anisotropy factor g and light irradiation angle $\alpha$ that are assumed to be known. To calculate the numerical distribution $I(\rho, \mu_s, \mu_a)$, the surface of the matrix is subdivided into partial areas. As the result of the simulation calculation, a two-dimensional table of I values as a function of $\rho_i$ and $\mu_{a,k}$ is obtained.

There is no need to perform separate calculations for the various absorption values. Rather, the absorption probability can be calculated for each photon for various $\mu_a$ values on the basis of its path length and expressed by means of a respective "weight" of the photon. For data reduction and in order to provide for more rapid calculations, a non-linear least squares fit is performed for each partial area of the surface, whereby the calculated values for various absorption values are used to determine the parameters, a and b, of equation (2).

By means of this procedure, values for the intensity $I(\rho_i)$ and the coefficients $a(\rho_i)$ and $b(\rho_i)$ of equation (2) are obtained for each measuring distance $\rho_i$ used in the calculation; these values must be stored in the form of a lookup table. This lookup table is then used in step c of the algorithm (including partial steps c1 to c3) for instance as follows:

For each value of $\mu_s$, for which an intensity profile is required, a scaling factor s is calculated according to $s = \mu_{s,MC}/\mu_s$.

The values of $\rho_i$ are scaled with this factor:

$$\rho_i' = \rho_i \cdot s$$

The scaling of $\rho$ leads to a change of the size of the partial areas of the matrix surface that is employed in the simulation. Therefore, the intensity measurement values must be adjusted accordingly: $I_0'(\rho_i') = I_0(\rho_i)/s^2$.

The attenuation due to absorption is taken into consideration by scaling $\mu_a$ according to $\mu_a' = \mu_a \cdot s$. The resulting values $\mu_a$ and $\rho_i$ are then inserted into equation (2) in order to calculate a theoretical intensity profile $I(\rho_i, \mu_s, \mu_a)$. An interpolation is performed, if the values of $\rho_i$ used therein do not agree with the measuring distances.

These calculations are performed for a large number of values of the parameters $\mu_s$, $\mu_a$, $\rho$, and then compared to the measured values. The optimal values of the parameters are determined by a non-linear least squares fit.

The invention claimed is:

1. A method for determination of a light transport parameter characteristic of light scattering in skin tissue, the method comprising:

irradiating light at a light irradiation site in at least three detection measurements;

irradiating the light as a primary light at the light irradiation site into the skin tissue through a surface by means of a light-guiding element, wherein the light-guiding element contacts the surface of the skin tissue at the light irradiation site;

irradiating the primary light into the skin tissue at the light irradiation site obliquely at a light irradiation angle between 5° and 85° relative to a normal on the surface;

detecting light exiting the skin tissue through the surface as a secondary light at a detection site that is located in the at least three detection measurements at different measuring distances from the respective light irradiation site;

measuring an intensity value of the secondary light;

evaluating the light transport parameter which is characteristic of the light scattering in the skin tissue, wherein the light transport parameter is derived by means of an evaluation algorithm from the intensity values measured in the detection measurements, and wherein in at least two of said detection measurements, the measuring distance between the respective light irradiation site and the respective detection site corresponds to no more than approximately 3.5 mm.

2. The method of claim 1, wherein in at least three detection measurements, the measuring distance between the respective light irradiation site and the respective detection site corresponds to no more than approximately 3.5 mm.

3. The method of claim 1, wherein said at least three detection measurements includes at least four detection measurements and wherein in said at least four detection measurements, the measuring distance between the respective light irradiation site and the respective detection site corresponds to no more than approximately 3.5 mm.

4. The method of claim 1, wherein said only intensity measurement values resulting from detection measurements, in which the measuring distance between the respective light irradiation site and the respective detection site corresponds to no more than approximately 7.0 mm, are included in the evaluation step.

5. The method of claim 1, wherein the detection step comprises detecting the secondary light by means of a light-guiding element which contacts the skin tissue at the detection site.

6. The method of claim 1, wherein the detection step comprises detecting the secondary light at the detection site in a detection direction that runs oblique to the surface, at an angle between 5° and 85° relative to a normal on the surface.

7. The method of claim 6, wherein the detection direction is oriented towards the light irradiation site.

8. The method of claim 6, wherein the secondary light is detected on the surface of the skin tissue at a plurality of detection fields each of which comprises a plurality of detection sites, the detection direction being the same for the plurality of detection sites of a detection field, but different for the plurality of detection fields.

9. A method for the determination of an analyte in a biological matrix, the method comprising:

irradiating light at a light irradiation site in at least three detection measurements;

irradiating the light as a primary light at the light irradiation site into the biological matrix through a surface by means of a light-guiding element, wherein the light-guiding element contacts the surface of the biological matrix at the light irradiation site;

irradiating the primary light into the biological matrix at the light irradiation site obliquely at a light irradiation angle between 5° and 85° relative to a normal on the surface;

detecting light exiting the biological matrix through the surface as a secondary light at a detection site that is located in the at least three detection measurements at different measuring distances from the respective light irradiation site;

measuring an intensity value of the secondary light; and an evaluation step, wherein the concentration of the analyte in the biological matrix is derived by means of an evaluation algorithm from the intensity values measured of the secondary light in the detection measurements, wherein in at least two detection measurements, the measuring distance between the respective light irradiation site and the respective detection site corresponds to no more than approximately 3.5 mm.

10. The method of claim 9, wherein in at least three detection measurements, the measuring distance between the respective light irradiation site and the respective detection site corresponds to no more than approximately 3.5 mm.

11. The method of claim 9, wherein in at least four detection measurements, the measuring distance between the respective light irradiation site and the respective detection site corresponds to no more than approximately 3.5 mm.

12. The method of claim 9, wherein only intensity measurement values resulting from detection measurements, in which the measuring distance between the respective light irradiation site and the respective detection site corresponds to no more than approximately 7.0 mm, are included in the evaluation step.

13. The method of claim 9, wherein the detection step comprises detecting the secondary light by means of a light-guiding element which contacts the skin tissue at the detection site.

14. The method of claim 9, wherein the detection step comprises detecting the secondary light at the detection site in a detection direction that runs oblique to the surface, at an angle between 5° and 85° relative to a normal on the surface.

15. The method of claim 14, wherein the detection direction is oriented towards the light irradiation site.

16. The method of claim 14, wherein the secondary light is detected on the surface of the skin tissue at a plurality of detection fields each of which comprises a plurality of detection sites, the detection direction being the same for the plurality of detection sites of a detection field, but different for the plurality of detection fields.

17. The method of claim 9, wherein in at least two of said detection measurements, the measuring distance between the respective light irradiation site and the respective detection site corresponds to no more than approximately 3.5 mm.

18. A method for determination of a light transport parameter which is characteristic of light scattering in skin tissue, in particular for the purpose of determination of the concentration of glucose in the skin tissue, the method comprising:

irradiating light at a light irradiation site in at least three detection measurements;

irradiating the light as a primary light into the skin tissue through a surface;

irradiating the primary light into the skin tissue at the light irradiation site obliquely at a light irradiation angle between 5° and 85° relative to a normal on the surface;

detecting light exiting the skin tissue through the surface as a secondary light at a detection site that is located in the at least three detection measurements at different measuring distances from the respective light irradiation site;

measuring an intensity value of the secondary light; and an evaluating step, in which the light transport parameter which is characteristic of the light scattering in the skin tissue is derived by means of an evaluation algorithm from the intensity values measured in the detection measurements, wherein the evaluation algorithm includes the following steps:
(a) determining by means of a numerical simulation for a typical value of optical scattering ($\mu s, MC$) the theoretical dependence of the intensity (I) of the secondary light from the measuring distance ($\rho$) and the optical absorption ($\mu a$);
(b) storing the result of the simulation as a lookup table by which an intensity value (I($\rho, \mu a$)) is assigned to predetermined values of the measuring distance ($\rho$) and optical absorption ($\mu a$); and
(c) determining the parameter ($\mu s$) which is characteristic of the light scattering in the skin tissue by means of a fit procedure, in which for a plurality of different values of the light transport parameters ($\mu a, \mu s$) characterizing the light transport in the skin tissue the dependence of the intensity (I) on the measuring distance ($\rho$) is calculated and the result is compared to the intensity measurement values measured in the detection measurements in order to determine those values of the light transport parameters ($\mu a, \rho s$) at which an optimal agreement of the calculated dependence of the intensity (I) on the measuring distance ($\rho$) and the respective intensity measurement values is achieved, wherein step c) comprises the following substeps:
c1) calculating a scaling factor (s) from the relation of any selected optical scattering value ($\mu s$) to the typical optical scattering ($\mu s, MC$) used in step a);
c2) converting the independent variables ($\rho, \mu a$) of the lookup table stored in step b) by means of the scaling factor (s);
c3) calculating the dependence of the intensity (I) on the optical absorption ($\mu a$) and the measuring distance ($\rho$) at the selected optical scattering value ($\mu s$) by means of the converted variables on the basis of the values stored in the lookup table.

19. The method according to claim 18, wherein the detection measurements are performed by means of a portable analysis instrument which includes a first computer system for performing a part of the evaluation algorithm, wherein steps a) and b) are performed by a second computer system which is separate from the portable analysis instrument.

20. A device for determination of a light transport parameter which is characteristic of light scattering in skin tissue, in particular for the purpose of determination of the concentration of glucose in the skin tissue, the device comprising:
a measuring head having at least one light irradiation means for irradiating the primary light at at least one light irradiation site and at least one detection means for detecting the secondary light at at least one detection site;
wherein the at least one irradiation site and the at least one detection site are arranged such that their measuring distance ($\rho$) is not more than approximately 3.5 mm; and
wherein the light irradiation means includes a light-guiding element that contacts the surface of the skin tissue at the selected light irradiation site and are arranged in such a manner that the primary light is irradiated into the skin tissue obliquely at the light irradiation site at a light irradiation angle between 5° and 85° relative to a normal on the surface.

* * * * *